US012635898B2

(12) United States Patent
Park et al.

(10) Patent No.: US 12,635,898 B2
(45) Date of Patent: May 26, 2026

(54) IMPLANTED ELECTRODE CONTROL DEVICE

(71) Applicant: SAMSUNG LIFE PUBLIC WELFARE FOUNDATION, Seoul (KR)

(72) Inventors: Eun Kyoung Park, Seoul (KR); Tae Kyung Kim, Seoul (KR); Young Min Shon, Seoul (KR); Kyu Sung Lee, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 177 days.

(21) Appl. No.: 17/925,721

(22) PCT Filed: Mar. 30, 2021

(86) PCT No.: PCT/KR2021/003932
§ 371 (c)(1),
(2) Date: Nov. 16, 2022

(87) PCT Pub. No.: WO2021/235675
PCT Pub. Date: Nov. 25, 2021

(65) Prior Publication Data
US 2023/0346250 A1 Nov. 2, 2023

(30) Foreign Application Priority Data
May 18, 2020 (KR) ........................ 10-2020-0059110

(51) Int. Cl.
*A61B 5/06* (2006.01)
*A61N 1/05* (2006.01)

(52) U.S. Cl.
CPC ............ *A61B 5/061* (2013.01); *A61N 1/0534* (2013.01)

(58) Field of Classification Search
CPC ......................... A61B 34/10; A61B 2034/107
See application file for complete search history.

(56) References Cited

U.S. PATENT DOCUMENTS

| | | | |
|---|---|---|---|
| 8,725,235 B2 | 5/2014 | Gielen et al. | |
| 2012/0184844 A1* | 7/2012 | Gielen ................... | A61B 5/062 600/424 |

(Continued)

FOREIGN PATENT DOCUMENTS

| | | |
|---|---|---|
| JP | 4717683 B2 | 7/2011 |
| KR | 10-2015-0073513 A | 7/2015 |

(Continued)

OTHER PUBLICATIONS

Office Action in KR Patent Application No. 10-2023-0001665 dated Feb. 26, 2024.

(Continued)

*Primary Examiner* — Serkan Akar
*Assistant Examiner* — Gabriel Victor Popescu
(74) *Attorney, Agent, or Firm* — Dilworth IP, LLC

(57) ABSTRACT

A method of controlling an implanted electrode includes receiving information from an external device; calculating a first region in a body in which the electrode is to be implanted and a second region in which electrode implantation is prohibited, based on the received information; and calculating a plurality of predicted paths through which an electrode is moved based on the first region or the second region, and outputting the plurality of predicted paths.

8 Claims, 12 Drawing Sheets

Electrode moving UI

(56) References Cited

U.S. PATENT DOCUMENTS

| | | | |
|---|---|---|---|
| 2013/0150934 A1 * | 6/2013 | Bucholz | A61N 1/0534 |
| | | | 607/116 |
| 2016/0136443 A1 | 5/2016 | Grandhe et al. | |
| 2019/0298988 A1 * | 10/2019 | Monteiro | A61N 1/0534 |
| 2019/0321106 A1 | 10/2019 | Bergman et al. | |
| 2022/0015684 A1 * | 1/2022 | Tatum | A61N 1/0529 |

FOREIGN PATENT DOCUMENTS

| | | |
|---|---|---|
| KR | 101549786 B1 | 9/2015 |
| KR | 10-2016-0068922 A | 6/2016 |

OTHER PUBLICATIONS

International Search Report of WIPO in Application No. PCT/KR2021/003932, filed Mar. 30, 2021.

Office Action in related Korean patent application No. 10-2020-0059110 with English translation, dated Nov. 17, 2022, 6 pages.

* cited by examiner

Enlarged electrode moving UI

Enlarged electrode width change UI

IMPLANTED ELECTRODE CONTROL DEVICE

FIELD OF THE INVENTION

The present invention relates to a method of controlling an implanted electrode used in surgery for implanting an electrode into the body and a control device using the same, and more particularly, to a method of controlling a position of an electrode implanted into the body and a control device using the same.

BACKGROUND OF THE INVENTION

Recently, with an aging population, the number of patients with movement disorders caused by abnormalities in nerve cells, such as Parkinson's disease, is increasing. Parkinson's disease is a disease in which nerve cells that secrete dopamine in a specific region of the brain called the substantia nigra located in the midbrain are gradually lost for unknown causes. In patients with Parkinson's disease, symptoms such as tremor (slow movement), tremors at rest, muscle stiffness, and postural instability occur.

As a treatment for Parkinson's disease, the patient needs to first start drug treatment and continue to take the drug. Drug treatment does not cure Parkinson's disease or stop the progression of Parkinson's disease, but only uses drugs that supplement the lack of dopamine so that the patient can do well in daily life. Currently, drugs that regenerate dopaminergic neurons or delay the loss of dopaminergic neurons have not yet been developed. Although drug treatment is effective in most patients with Parkinson's disease, side effects such as dyskinesia or motor fluctuations (sometimes called wearing off) begin to occur when about 3 to 5 years have elapsed after drug treatment. Some patients enter a stage where daily life is difficult with medication alone. Surgical treatment is required for patients at this stage, and the most commonly performed surgical treatment is deep brain stimulation.

Deep brain stimulation is an operation in which an electrode is implanted into a specific region of the brain and then connected to an electrical stimulator implanted in the body to continuously electrically stimulate the specific region of the brain. In deep brain stimulation, an electrode is implanted into the brain, an electric wire is connected to the electrode, a microcurrent is sent to the lesion, and an abnormal brain neural circuit may be restored by continuously stimulating the brain with electricity.

On the other hand, epilepsy, another movement disorder, has an epileptic seizure as a symptom, and the epileptic seizure is a central symptom caused by various factors such as focal brain lesions, systemic metabolic disorders, drug addiction, hypoxia, head trauma, or extreme overwork and lack of sleep.

For the diagnosis of epilepsy, primary epilepsy tests such as video electroencephalography (EEG), magnetic resonance imaging (MRI), single-photon emission computed tomography (SPECT), positron emission tomography (PET), or magnetoencephalography (MEG) may be performed, electrode implantation may be performed to implant electrodes into the cranial cavity through information obtained from the primary epilepsy test, and secondary epilepsy test may be performed with information obtained from electrode implantation. An EEG may be recorded through an electrode implanted into the cranial cavity, and a region where an epileptic wave is detected from a cortical EEG at a specific position may be identified. Based on information obtained from the secondary epilepsy test, resection of an abnormal region may be performed.

In deep brain stimulation or electrode implantation, how accurately an electrode is implanted into a specific region of the brain and how an electrode is implanted along a stable path are most important, so an operator needs to monitor an implantation position and an implantation path of an electrode in real time.

SUMMARY OF THE INVENTION

The present invention provides a method of controlling an implanted electrode and a control device using the same to provide image information about a position of an electrode implanted into the body in real time.

The present invention further provides image information about a path through which an electrode is implanted into the body.

As an embodiment of the present disclosure, a method of controlling an implanted electrode may be provided.

The method according to an embodiment of the present disclosure may include: receiving information from an external device; calculating a first region in a body in which an electrode is to be implanted and a second region in which electrode implantation is prohibited, based on the received information; and calculating a plurality of predicted paths through which an electrode is moved based on the first region or the second region, and outputting the plurality of predicted paths.

The method according to an embodiment of the present disclosure may further include the external device comprises at least one of a video electroencephalography (EEG) device, a magnetic resonance imaging (MRI) examination device, a single-photon emission computed tomography (SPECT) examination device, a positron emission tomography (PET) device, a magnetoencephalography (MEG) device, and a C-arm device.

The method according to an embodiment of the present disclosure may further include calculating a type of electrode to be implanted into a body based on the received information; or receiving the type of electrode to be implanted into a body.

The method according to an embodiment of the present disclosure may further include identifying a real-time position of an electrode pre-implanted into a body based on the received information, and outputting the identified real-time position of the electrode.

The method according to an embodiment of the present disclosure may further include calculating each of the plurality of predicted paths differently based on the second region and the type of electrode.

As an embodiment of the present disclosure, an implanted electrode control device may be provided.

The device according to an embodiment of the present disclosure may include: a communication unit configured to receive information from an external device; a control unit configured to calculate a first region in a body in which an electrode is to be implanted and a second region in which electrode implantation is prohibited, based on the received information, and to calculate a plurality of predicted paths through which an electrode is moved based on the first region or the second region; and an output unit configured to output the plurality of predicted paths.

The device according to an embodiment of the present disclosure may further include the external device comprises at least one of a video electroencephalography (EEG) device, a magnetic resonance imaging (MRI) examination device, a single-photon emission computed tomography (SPECT) examination device, a positron emission tomography (PET) device, a magnetoencephalography (MEG) device, and a C-arm device.

The device according to an embodiment of the present disclosure may further include the control unit calculates a type of electrode implanted into a body based on the received information.

The device according to an embodiment of the present disclosure may further include the communication unit receives a type of electrode implanted into a body.

The device according to an embodiment of the present disclosure may further include the control unit identifies a real-time position of an electrode pre-implanted into a body based on the received information, and the output unit outputs the identified real-time position of the electrode.

The device according to an embodiment of the present disclosure may further include the control unit calculates each of the plurality of predicted paths differently based on the electrode and the type of electrode.

A method and a device for controlling an implanted electrode according to the present invention having the configuration as described above output an implantation region of an electrode that generates optimal electrical stimulation through a real-time image, so that a user performing electrode implantation surgery may monitor a real-time situation, thereby stably inducing the electrode implantation surgery.

In addition, the method and the device for controlling an implanted electrode according to the present invention may prevent side effects that may occur in electrode implantation surgery by providing a moving path of an electrode implanted into the body and a region where electrode implantation is prohibited.

In addition, the method and the device for controlling an implanted electrode according to the present invention may provide a variety of cases for electrode implantation surgery by outputting a simulation image including moving paths of different electrodes according to types of electrodes implanted into the body.

DETAILED DESCRIPTION OF THE INVENTION

Figure 1:
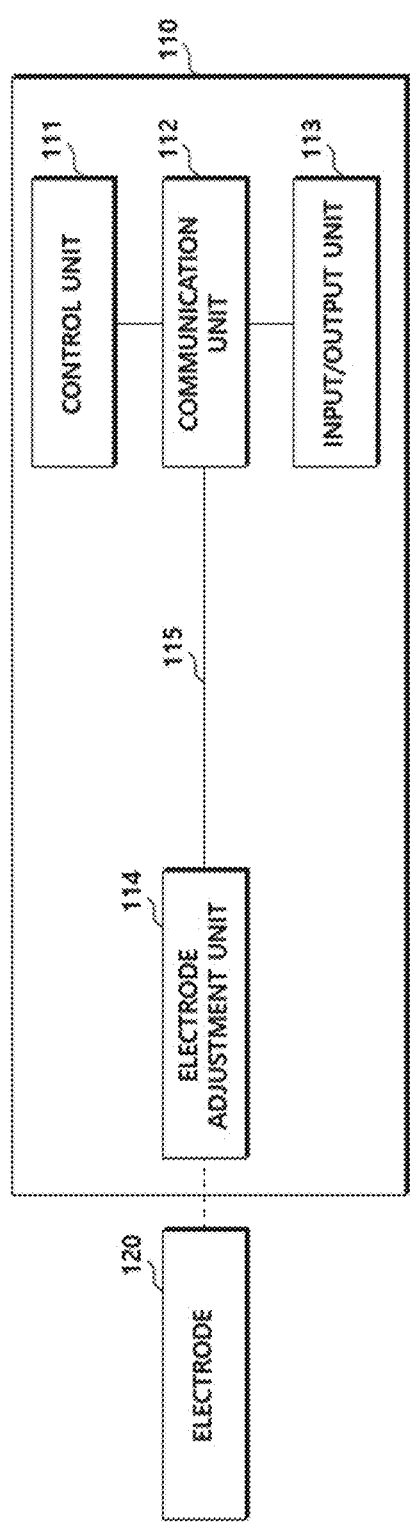
FIG. 1 is a schematic diagram for explaining an implanted electrode control device according to an embodiment of the present invention.

Hereinafter, the terms used in the specification will be briefly described, and the configuration and operation of a preferred embodiment of the present invention will be described in detail as a detailed description for carrying out the present invention.

General and widely used terms have been employed herein, in consideration of functions provided in the present invention, and may vary according to an intention of one of ordinary skill in the art, a precedent, or emergence of new technologies. In addition, in certain cases, a term which is not commonly used can be selected. In such a case, the meaning of the term will be described in detail at the corresponding portion in the description of the present invention. Therefore, the terms used herein should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, terms such as " . . . unit", " . . . module", or the like described herein refer to units that perform at least one function or operation, and the units may be implemented as hardware or software or as a combination of hardware and software. In addition, throughout the specification, when an element is "connected" to another element, the elements may not only be "directly connected", but may also be "electrically connected" via another element therebetween.

Reference will now be made in detail to embodiments, examples of which are illustrated in the accompanying drawings. In this regard, the present invention may have different forms and should not be construed as being limited to the descriptions set forth herein. In addition, descriptions of well-known functions and constructions will be omitted for clarity and conciseness, and similar reference numerals are assigned to similar elements throughout the specification.

Movement disorders refer to diseases including symptoms in which movement of parts (e.g., arms, legs, etc.) of the body is impaired, the body cannot move as quickly as desired, or movements that are unintentional to one's will interfere with daily life due to abnormalities in the central and peripheral nervous systems. The movement disorders include disorders in which movement is abnormally reduced or increased without paralysis, or in which abnormal movement occurs. Among diseases belonging to movement disorders, representative diseases include Parkinson's disease, essential tremor (tremor), dystonia, and other diseases such as tremor, Wilson's disease, muscle spasms, paroxysmal dyskinesia, unilateral facial spasm, blepharospasm, tics, gait disorders such as ataxia, progressive supranuclear palsy, multiple system atrophy, Huntington's disease, chorea, and torticollis.

Most movement disorders cannot be cured fundamentally, and the primary treatment for symptom relief is drug treatment, but it is not very effective except for Parkinson's disease. Even in the case of Parkinson's disease, if drug treatment is continued, the effect of the drug fluctuates significantly over time, and due to side effects such as dyskinesia caused by drugs, pain caused by drugs, gastrointestinal disorders, psychiatric symptoms, etc., there may be cases in which symptoms cannot be controlled satisfactorily with drug treatment. As a treatment in this case, there is a surgical treatment called deep brain stimulation that implants an electrode that gives electrical stimulation to the deep brain. The deep brain stimulation may be applied not only to movement disorders, but also in rare cases to obsessive-compulsive disorders, intractable depression, and epilepsy.

Deep brain stimulation is a treatment method that applies an appropriate electrical signal to a target point in the deep brain that controls movement. An electrode and a soft, thin wire are implanted through the skull and deep into the brain. The battery that supplies the power is connected to the wire and implanted into the hidden skin. The electrode is usually implanted into one of the basal ganglia (nerve centers deep in the brain that are thought to cause spastic torticollis) through the skull. After surgery, the frequency and power of electrical stimulation are adjusted.

On the other hand, the deep brain stimulation is an example that may be applied to a method and a device for controlling an implanted electrode according to an embodiment of the present invention. The method and device for controlling an implanted electrode according to an embodiment of the present invention may be applied to any electrode implantation surgery in which an electrode is implanted into the body. Hereinafter, surgery for implanting an electrode into the body is collectively referred to as electrode implantation surgery (electrode implantation).

Conventionally, for the treatment of movement disorders, abnormal movement is blocked by destroying a region with nerve abnormalities, but in this case, there is a disadvantage in that the brain tissue is damaged. Electrode implantation surgery is a surgical method that balances abnormal brain functions by implanting an electrode into a specific region of the brain and allowing current to flow. The electrode implantation surgery provides microscopic electrical stimulation to fundamentally block only abnormal brain signals that cause dysfunction without destroying nerve cells. A stimulation generator (battery) stimulates the electrode of the brain so that the patient may live his or her daily life without any major abnormalities. The stimulation generator may be implanted into the clavicle.

Electrode implantation surgery is a treatment method with minimal damage to the brain, and an optimal method of electrical stimulation for each patient may be found and applied. The electrode implantation surgery includes implanting an electrode and a signal generator. In particular, a process of implanting an electrode into the brain is the most important part that determines the success or failure of surgery, and a technique called microelectrode measurement may be used to increase the accuracy of surgery.

For detailed examination before the electrode implantation surgery, surgery to implant an electrode into a region to be examined may be performed, and video-electroencephalography and brain function tests may be re-performed using pre-implanted electrodes. Surgery to implant an electrode into the body is an operation of implanting an electrode into a region where epilepsy is expected to occur, and various types of electrodes may be implanted.

Special electrodes may be implanted into the brain through the electrode implantation surgery, and the implanted electrodes include a subdural electrode, a depth electrode, and the like. The subdural electrode is embedded in a small, thin plastic plate and may be surgically implanted to be located on the brain surface. The depth electrode is a very thin and long electrode that may be implanted deep into the brain and directly measure the electrical activity of the brain. Based on the measured electrical activity, a target region into which an electrode will be implanted is accurately calculated, so that the electrode may be implanted along the safest path through surgery.

Video electroencephalography (EEG) may use an electrode in the brain through surgery, and a brain function test is to confirm a position between an epilepsy site and an important function of the brain using an electrode in the brain. Through this process, after determining an epilepsy site, the final surgery to safely remove the epilepsy lesion may be performed.

How accurately an electrode is implanted into a specific region of the brain and how stable an electrode is implanted through an implantation path are important in the electrode implantation surgery. Accordingly, a method of controlling an implanted electrode that provides an operator with an electrode position and an implantation path and a control device using the same will be described.

Hereinafter, the present invention will be described in more detail through embodiments. These embodiments are only for illustrating the present invention in more detail, and it will be apparent to one of ordinary skill in the art that the scope of the present invention is not limited by these examples according to the gist of the present invention.

FIG. 1 is a structural diagram for explaining an implanted electrode control device according to an embodiment of the present invention.

Referring to FIG. 1, an implanted electrode control device 110 according to an embodiment may control an electrode 120 to be implanted into the body. The implanted electrode control device 110 may include an electrode adjustment unit 114 that adjusts an electrode clamp that picks up the electrode 120 and implants the electrode 120 into the body, a communication unit 112 that transmits information about movement of the electrode 120 to the electrode adjustment unit 114, the electrode 120, an input/output unit 113 that outputs a region into which the electrode 120 is implanted, and a control unit 111 that generally controls them. The implanted electrode control device 110 according to an embodiment does not necessarily include all of the above-described components, but may include only some components.

The implanted electrode control device 110 according to an embodiment may output an image in which the electrode 120 is implanted into the body through the input/output unit 113 so that a user may check the implantation situation in real time, and may include a user interface (UI) capable of moving the electrode 120 or adjusting a distance between electrodes 120 through the electrode adjustment unit 114 at the same time or afterward.

The electrode adjustment unit 114 according to an embodiment may include an electrode clamp, and may be implanted into the body together with an electrode to change a position of the electrode 120 or a distance between contact points of the electrode 120 after electrode implantation surgery or deep brain stimulation surgery.

The implanted electrode control device 110 according to an embodiment may be applied to electrode implantation surgery or deep brain stimulation surgery. However, the implanted electrode control device 110 is not limited to surgery to implant an electrode into the brain, such as deep brain stimulation surgery, but is applied to various types of surgery to implant an electrode into the body other than the brain, for example, the spine or pelvis.

The implanted electrode control device 110 according to an embodiment may provide information about a position of the electrode 120 and information about a neural signal in a region into which the electrode 120 is implanted or a related region to a user through the input/output unit 113, and may analyze the neural signal through the control unit 111 to calculate an optimal region (stimulation position) into which the electrode 120 is implanted. The input/output unit 113 may output the stimulation position of the electrode 120 calculated by the control unit 111 through a display device.

The implanted electrode control device 110 according to an embodiment may move the electrode 120 through communication with the electrode adjustment unit 114 implanted into the body even after electrode implantation surgery. A specific method of moving the electrode 120 after electrode implantation surgery will be described in detail with reference to FIG. 2.

The implanted electrode control device 110 according to an embodiment may measure a neural signal adjacent to the electrode 120, and may include the communication unit 112 that transmits a command to move the electrode 120 considering the neural signal to the electrode adjustment unit 114.

The implanted electrode control device 110 according to an embodiment may analyze information received through the communication unit 112, such as a neural signal measured by the electrode 120, through the control unit 111, and may transmit a command for moving the electrode 120 generated by the control unit 111 to the electrode adjustment unit 114 through the communication unit 112.

In addition, the implanted electrode control device 110 according to an embodiment may include the input/output unit 113 for outputting a nerve signal, an image of an electrode implantation region in the body through MRI and CT (CT & MR co-registered image), a current position of the electrode 120 (Actual position of electrode), a planned electrode implantation position (Planned position of electrode), a corrected electrode position according to simulation (Re-position of electrode), an angle of each point of the electrode 120 or an electrode contact position (Point angle or electrode width display), a screen setting icon (View icon), and an execution icon (Control icon). The input/output unit 113 may include a display device, and according to an embodiment, may include a touch screen capable of image output and user input.

According to an embodiment, the input/output unit 113 may output an enlarged image or a reduced image of a specific region.

Figure 2:
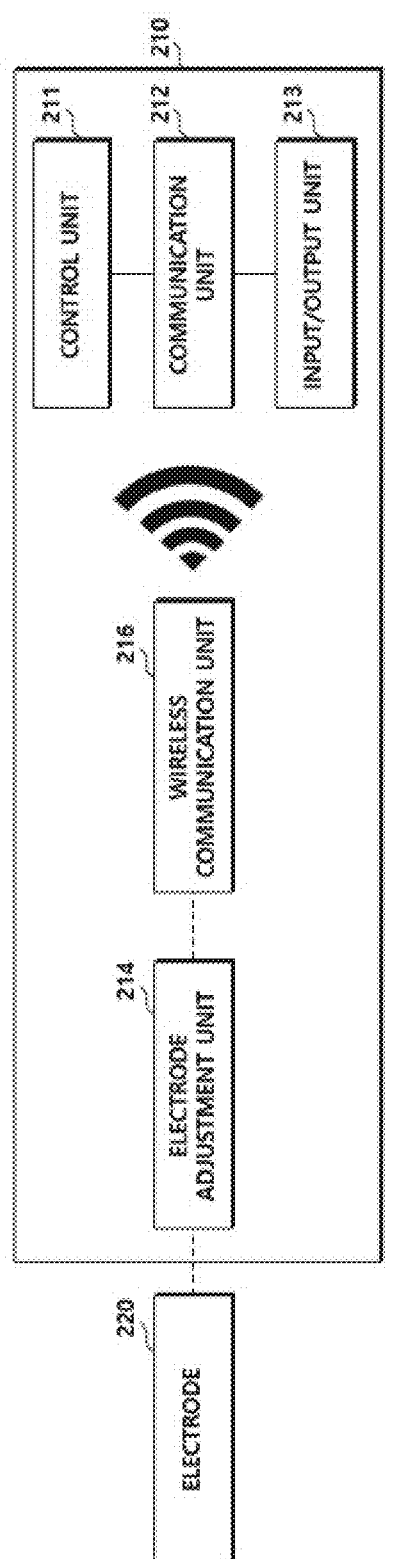
FIG. 2 is a schematic diagram for explaining an implanted electrode control device according to another embodiment of the present invention.

FIG. 2 is a structural diagram for explaining an implanted electrode control device according to another embodiment of the present invention.

Referring to FIG. 2, unlike the implanted electrode control device 110 according to FIG. 1, an implanted electrode control device 210 according to an embodiment may further include a wireless communication unit 216.

The communication unit 112 of the implanted electrode control device 110 according to FIG. 1 may transmit/receive a neural signal or a command for moving an electrode through wired communication with the electrode adjustment unit 114.

According to an embodiment, the wired communication may be at least one of communication using a universal synchronous/asynchronous receiver transmitter (USART), Inter-Integrated Circuit (I2C) communication, Serial Peripheral Interface (SPI) communication, and Controller Area Network (CAN) communication.

A communication unit 212 included in the implanted electrode control device 210 according to FIG. 2 may transmit and receive a neural signal or a command to move an electrode through wireless communication with an electrode adjustment unit 214 through the wireless communication unit 216. According to an embodiment, the wireless communication may be at least one of Bluetooth communication, Wireless Fidelity (WIFI) communication, and Low Frequency (LF) communication.

The electrode adjustment unit 114 included in the implanted electrode control device 110 according to FIG. 1 may be connected to the communication unit 112 by a cable 115. According to an embodiment, the communication unit 112 may transmit digitized data (e.g., a neural signal, etc.) to the control unit 111 through the cable 115 connected to the electrode control unit 114. The control unit 111 may transmit a control signal of the electrode 120 to the electrode adjustment unit 114 through the cable 115 based on data analyzed based on the data transmitted from the communication unit 112.

According to an embodiment, the cable 115 may be connected to the communication unit 112 through an electrode clip.

The wireless communication unit 216 of the implanted electrode control device 210 according to FIG. 2 may be integrated with the electrode adjustment unit 214. The wireless communication unit 216 may transmit and receive digitized data (e.g., a neural signal, etc.) generated from an electrode 220 or a control signal through wireless pairing with the communication unit 212.

When the communication unit 212 included in the implanted electrode control device 210 according to FIG. 2 transmits and receives a neural signal or a command to move an electrode through wireless communication with the electrode adjustment unit 214 through the wireless communication unit 216, the implanted electrode control device 210 may move the electrode 220 after electrode implantation surgery.

It is necessary to confirm an electrode position by synthesizing a CT image taken during a brain stabilization period after the electrode implantation surgery and the MRI image performed before the electrode implantation surgery. In addition, it is necessary to predict the degree of symptom improvement after the electrode implantation surgery, to find an optimal adjustment condition for a stimulation regulator of an electrode, or to change an electrode position.

After the electrode implantation surgery, a method of moving an electrode may be performed in the following order, but a method of controlling an implanted electrode according to an embodiment is not limited to the following order, and the order of some processes may be changed.

The electrode 120 and the electrode adjustment unit 114 may be in a state implanted into the body. A control unit 211 of the implanted electrode control device 210 may activate wireless communication with the electrode adjustment unit 114 implanted into the body together with the electrode 220 through the wireless communication unit 216.

After the wireless communication is activated, the control unit 211 may output a current position of the electrode 220 and an electrode implantation region using pre-stored information used in the previously performed electrode implantation surgery.

The control unit 211 may transmit a command to stop stimulation of the electrode 220 to the wireless communication unit 216, and when stimulation of the electrode 220 is stopped, may receive a neural signal detected from the pre-implanted electrode 220 through the wireless communication unit 216.

The control unit 211 may perform an analysis for specifying a region in which an electrode is to be located based on the received neural signal and image information input from an external device, and may recalculate an electrode implantation region.

The external device according to an embodiment may be at least one of a video EEG device, a magnetic resonance imaging (MRI) examination device, a single-photon emission computed tomography (SPECT) examination device, a positron emission tomography (PET) device, a magnetoencephalography (MEG) device, and a C-arm device (an X-ray video imaging device).

The control unit 211 may calculate a distance or direction from a current electrode position to the recalculated electrode implantation region to locate the electrode 220 in the recalculated electrode implantation region, and may calculate a moving path based on a distance or a direction to the recalculated electrode implantation region. The control unit 211 may output a simulation image of electrode movement by using the calculated moving path. A user may enlarge the simulation image through an input/output unit such as a mouse, and may input an input value for precisely adjusting electrode position movement based on the enlarged simulation image.

According to an embodiment, when the calculated moving path includes a region in which implantation of a pre-input electrode is prohibited, the control unit 211 may recalculate the moving path.

After the electrode position movement is performed, the control unit 211 may stop obtaining a neural signal detected from the electrode 220 and restart stimulation of an electrode.

When the electrode position movement is terminated after electrode implantation surgery by restarting the stimulation of an electrode, the control unit 211 may release wireless communication connection between the wireless communication unit 216 and the communication unit 212.

Figure 3:
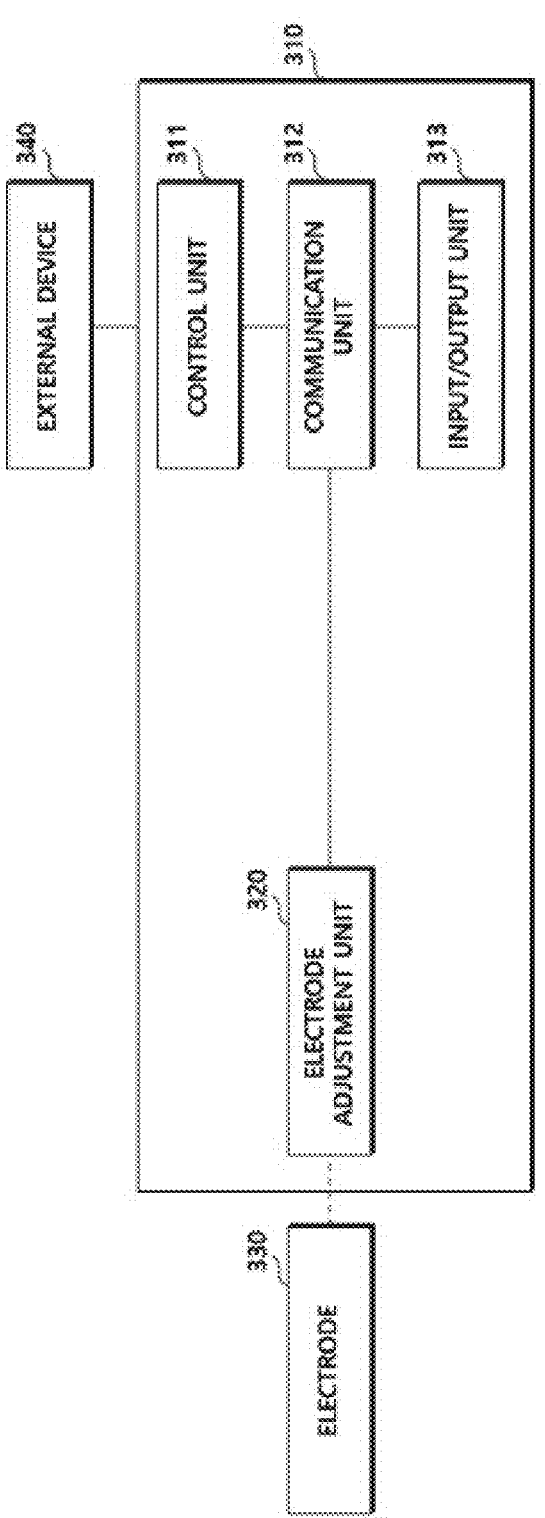
FIG. 3 is a schematic diagram for explaining an external device interworking with an implanted electrode control device according to an embodiment of the present invention.

FIG. 3 is a structural diagram for explaining an external device interworking with an implanted electrode control device according to an embodiment of the present invention.

Referring to FIG. 3, a control unit 311 of an implanted electrode control device 310 may calculate a region in which an electrode 330 is to be implanted as image information based on information received from an external device 340, and may output an image through an input/output unit 313 using the calculated image information. According to an embodiment, the information received from the external device 340 may be an image of an electrode implantation region in the body through MRI and CT (CT & MR co-registered image).

The control unit 311 of the implanted electrode control device 310 according to an embodiment may analyze characteristics of a C arm image and a neural signal received from a communication unit 312, overlap the position of the electrode 330 on a region in which the electrode 330 is to be implanted, and output the characteristics through the input/output unit 313.

The external device 340 according to an embodiment may be at least one of a video EEG device, an MRI examination device, a SPECT examination device, a PET device, an MEG device, and a C-arm device (an X-ray video imaging device).

Figure 4:
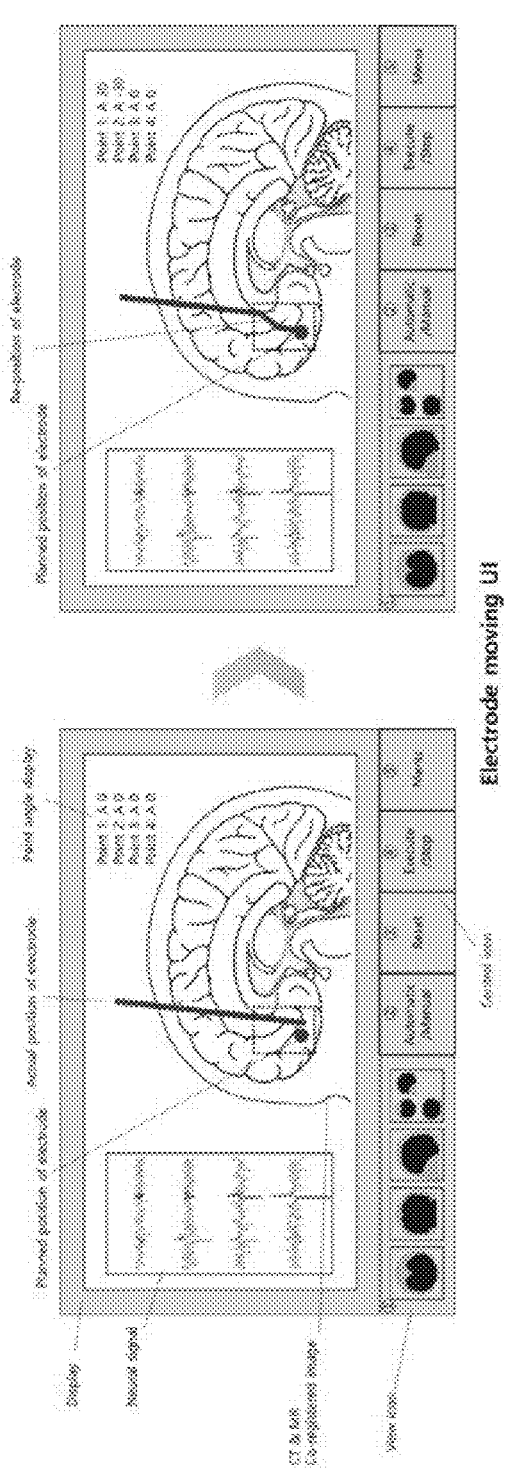
FIG. 4 is a pictorial view for explaining an output screen of an implanted electrode control device according to an embodiment of the present invention.

FIG. 4 is a view for explaining an output screen of an implanted electrode control device according to an embodiment of the present invention.

Referring to FIG. 4, the output screen of the implanted electrode control device may be an output screen of the input/output units 113, 213, and 313 of FIGS. 1 to 3.

The output screen of the input/output units 113, 213, and 313 may be output through a display device that outputs a real-time image of the body into which an electrode is to be implanted, and the input/output units 113, 213, and 313 may include a UI capable of user input.

In addition, the input/output units 113, 213, and 313 of the implanted electrode control device according to an embodiment may output a nerve signal, an image of an electrode implantation region in the body through MRI and CT (CT & MR co-registered image), a current position of the electrode (Actual position of electrode), a planned electrode implantation position (Planned position of electrode), a corrected electrode position according to simulation (Re-position of electrode), an angle of each point of the electrode 120 or an electrode contact position (Point angle or electrode width display), a screen setting icon (View icon), and an execution icon (Control icon).

According to an embodiment, the output screen may include a view icon ①, and a user may change an output direction of an electrode implantation region through the view icon ①.

According to an embodiment, the implanted electrode control device may output an electrode position in real time through the output screen, and a user may check the electrode position through the corresponding output screen. The implanted electrode control device may move the electrode to a correct position by simulating electrode movement or electrode contact point movement.

According to an embodiment, the output screen may include Automatic/Manual ②, a user may automatically simulate an electrode position through data obtained by analyzing position adjustment of the electrode and a target implantation position, or may manually adjust an electrode position using a mouse or touch screen.

According to an embodiment, the output screen may include Reset ③, and a user may initialize the simulated electrode position through Reset ③.

According to an embodiment, the output screen may include Execute/Stop ④, and a user may adjust the electrode position or stop the electrode movement as simulated through Execute/Stop ④.

According to an embodiment, the output screen may include Menu ⑤, and a user may select the type and model of an electrode to be used through Menu ⑤, output information about the patient, designate an electrode implantation position, or check information about a software program included in the implanted electrode control device.

Depending on the type and model of electrode, a method of movement after the first electrode implantation may be different. According to an embodiment, the implanted electrode control device may provide convenience by providing a simulation result to a user considering respective moving methods corresponding to the types and models of a plurality of electrodes already input.

The type of electrode according to an embodiment may include a general electrode, an electrode in which a contact point of the electrode may be changed, an electrode in which a position of the electrode is moved, an electrode in which a contact point of the electrode is moved, or the like.

According to the type and model of electrode according to an embodiment, only a depth of the electrode may be changed, a direction of the electrode may be changed by bending at each node of the electrode, or a position of a contact point of the electrode may be changed.

Figure 5:
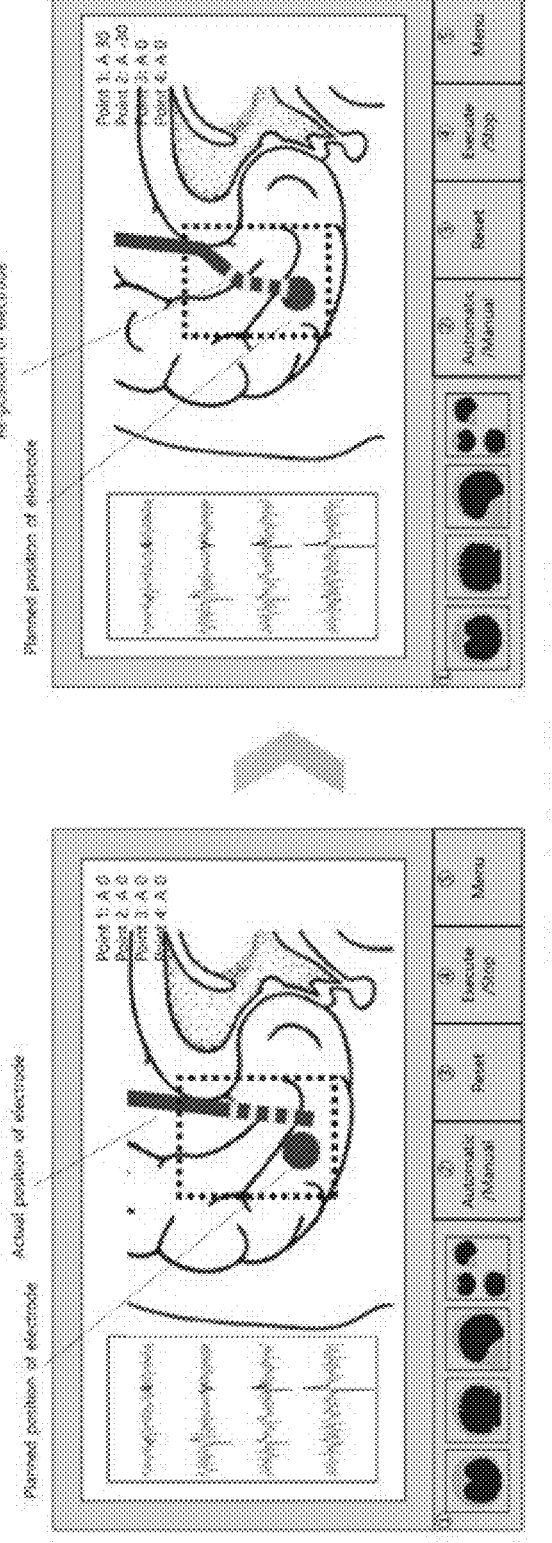
FIG. 5 is a pictorial view for explaining an enlarged output screen of an implanted electrode control device according to an embodiment of the present invention.

FIG. 5 is a view for explaining an enlarged output screen of an implanted electrode control device according to an embodiment of the present invention.

Referring to FIG. 5, compared with FIG. 4, the implanted electrode control device may enlarge and output a specific region of the output screen. Conversely, the implanted electrode control device may reduce and output a specific region of the output screen.

According to an embodiment, when receiving a mouse or touch input from a user, the implanted electrode control device may output an enlarged or reduced image of a specific region. However, the user input is not limited to the mouse or touch input, and may be changed according to the type of a user interface provided in the implanted electrode control device, such as a voice command.

Figure 6:
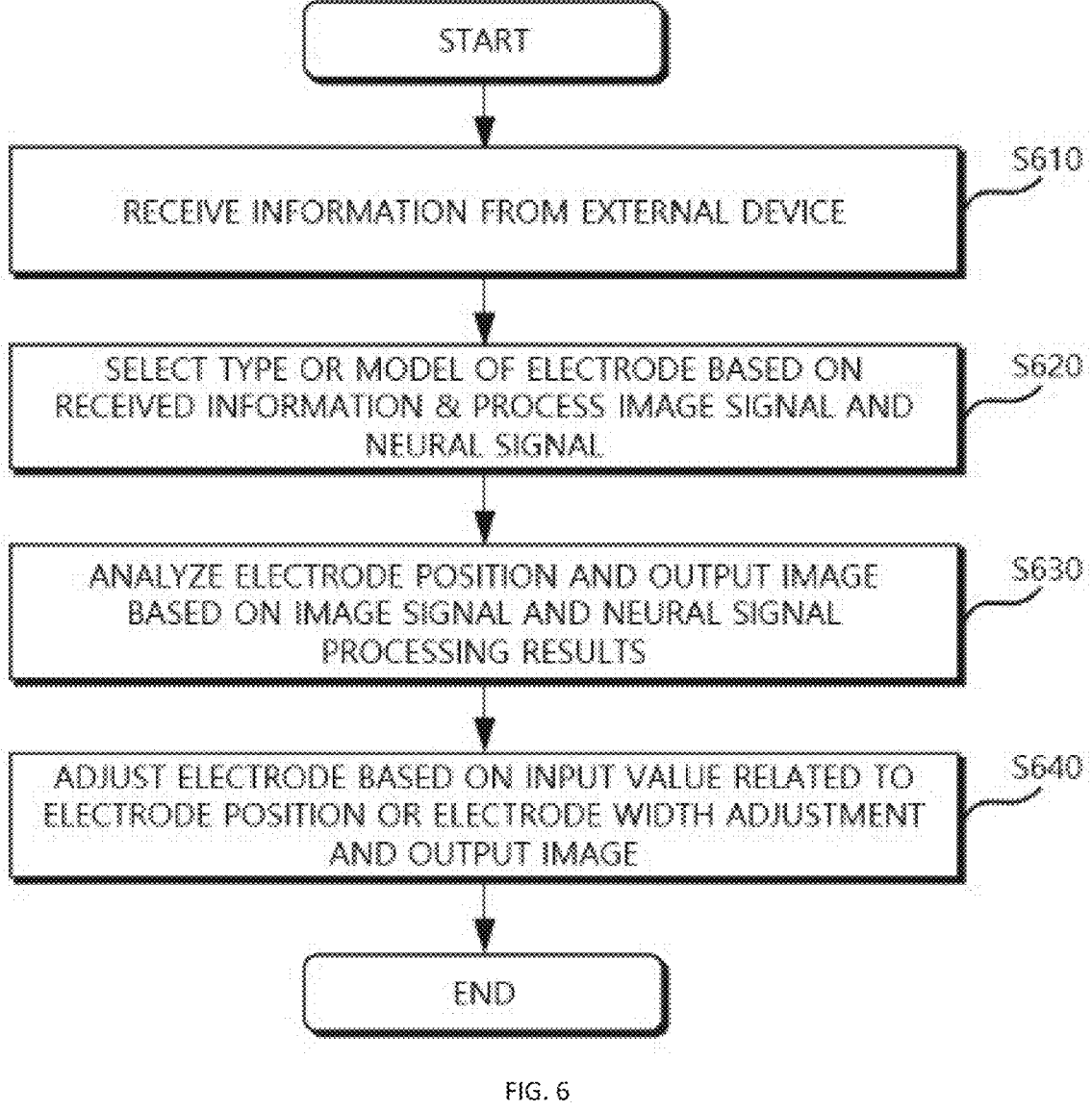
FIG. 6 is a flowchart illustrating a method of controlling an implanted electrode according to an embodiment of the present invention.

FIG. 6 is a flowchart illustrating a method of controlling an implanted electrode according to an embodiment of the present invention.

Referring to FIG. 6, in operation S610, the implanted electrode control device may receive information from an external device. According to an embodiment, the information received from the external device may be image information, and the implanted electrode control device may receive various types of image information from a plurality of external devices.

According to an embodiment, in operation S620, the implanted electrode control device may select the type or model of an electrode based on information received from an external device. According to an embodiment, the type or model of an electrode may be selected by a user. The implanted electrode control device may calculate an image signal by combining various types of image information received from an external device, and may calculate image information of an electrode implantation region based on the image signal.

According to an embodiment, in operation S630, the implanted electrode control device may receive a neural signal from a pre-implanted electrode to calculate digitized information, and may calculate image information based on the digitized information based on the neural signal.

According to an embodiment, the implanted electrode control device may calculate a real-time position of an electrode based on the image signal and the neural signal, and may output an image considering this.

According to an embodiment, in operation S640, the implanted electrode control device may generate a signal for directly adjusting an electrode based on an input value for adjusting a real-time position of an electrode or a width between contact points of the electrode, may adjust the real-time position of the electrode or the width between the contact points, and may output a real-time image.

Figure 7:
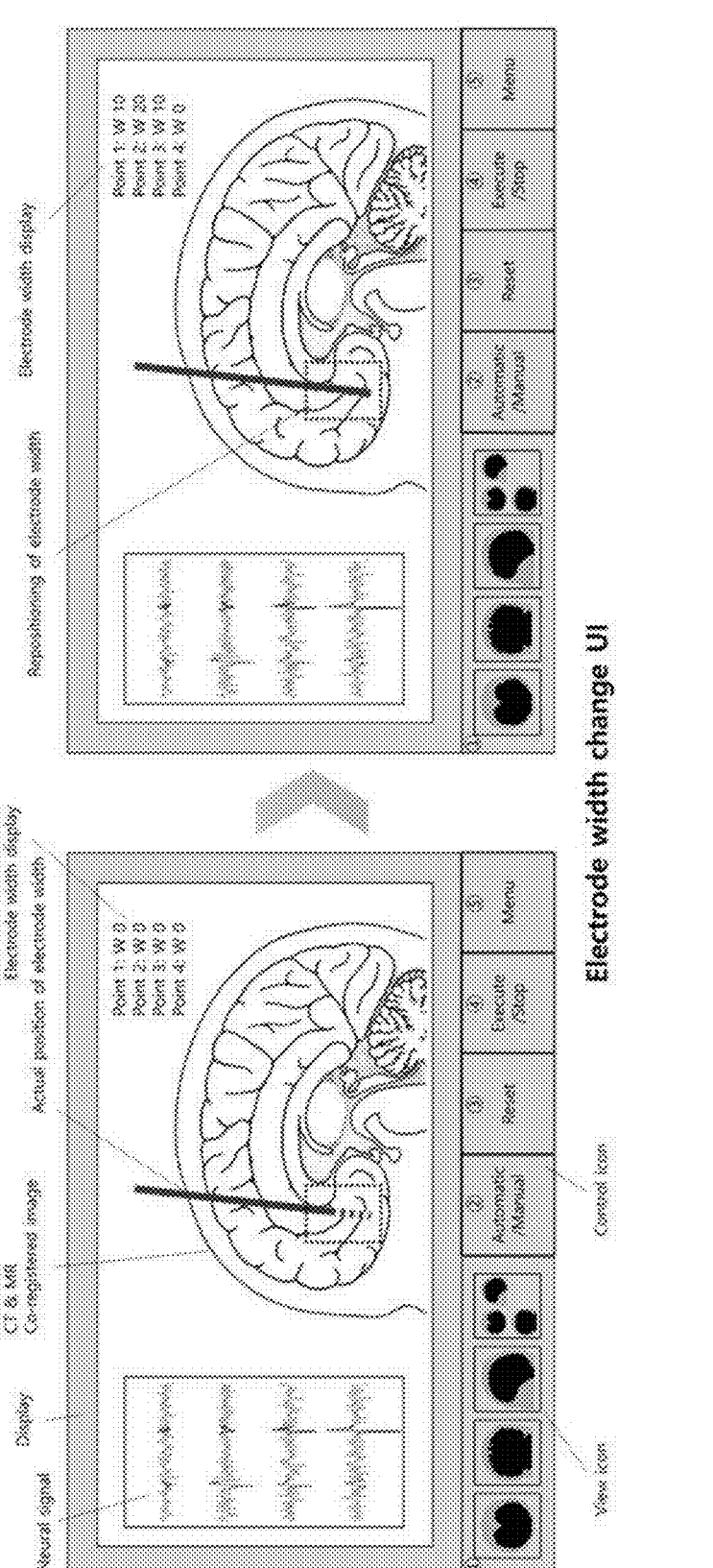
FIG. 7 is a pictorial view for explaining an image for adjusting a width between contact points of an electrode to be implanted, according to an embodiment of the present invention.
Figure 8:
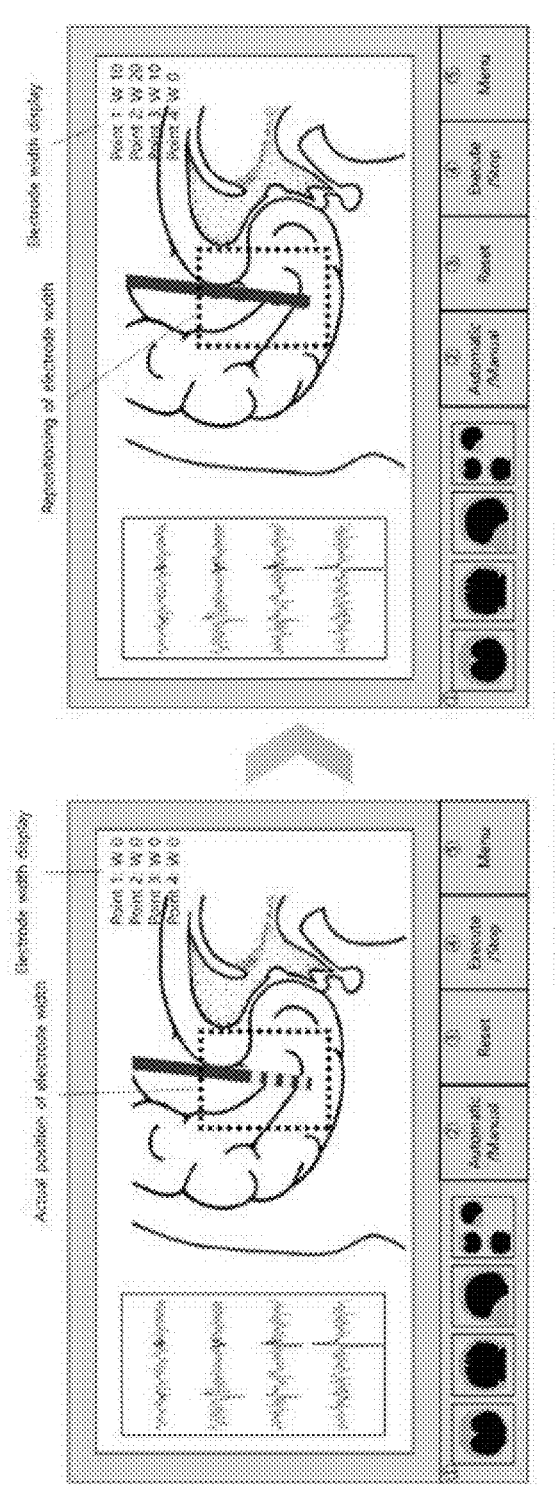
FIG. 8 is a pictorial view for explaining an image in which an image for adjusting a width between contact points of an electrode to be implanted is enlarged, according to an embodiment of the present invention.

FIG. 7 is a view for explaining an image for adjusting a width between contact points of an electrode to be implanted, according to an embodiment of the present invention, and FIG. 8 is a view for explaining an image in which an image for adjusting a width between contact points of an electrode to be implanted is enlarged, according to an embodiment of the present invention.

Referring to FIG. 7, a real-time image in which a width between contact points of an electrode is changed may be output.

Referring to FIG. 8, in order to more precisely adjust the width between the contact points of the electrode, a region in which the contact points of the electrode are located may be enlarged enough to be able to identify the width between the contact points of the electrode.

Figure 9:
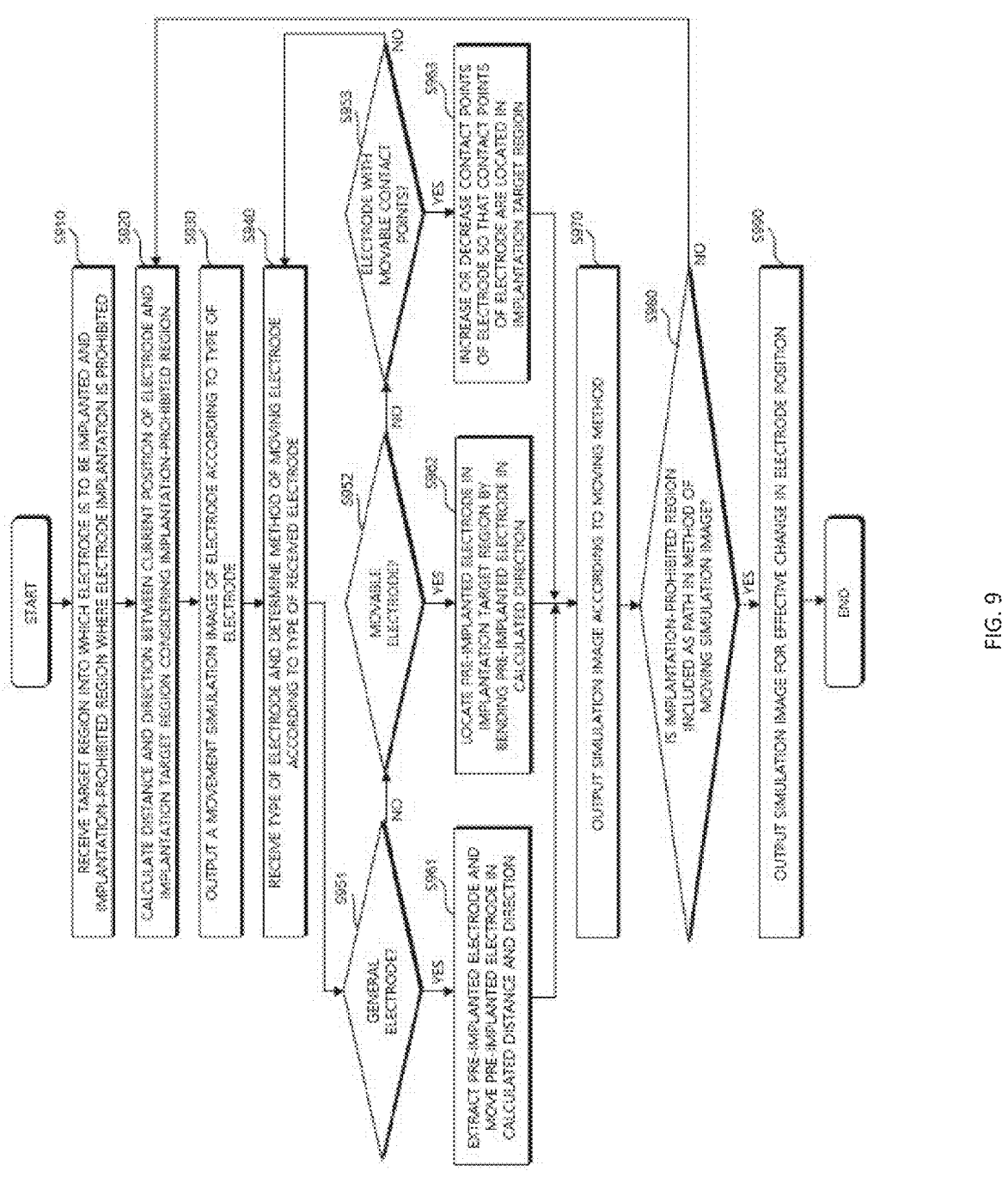
FIG. 9 is a flowchart for explaining a method of controlling an implanted electrode according to another embodiment of the present invention.
Figure 10:
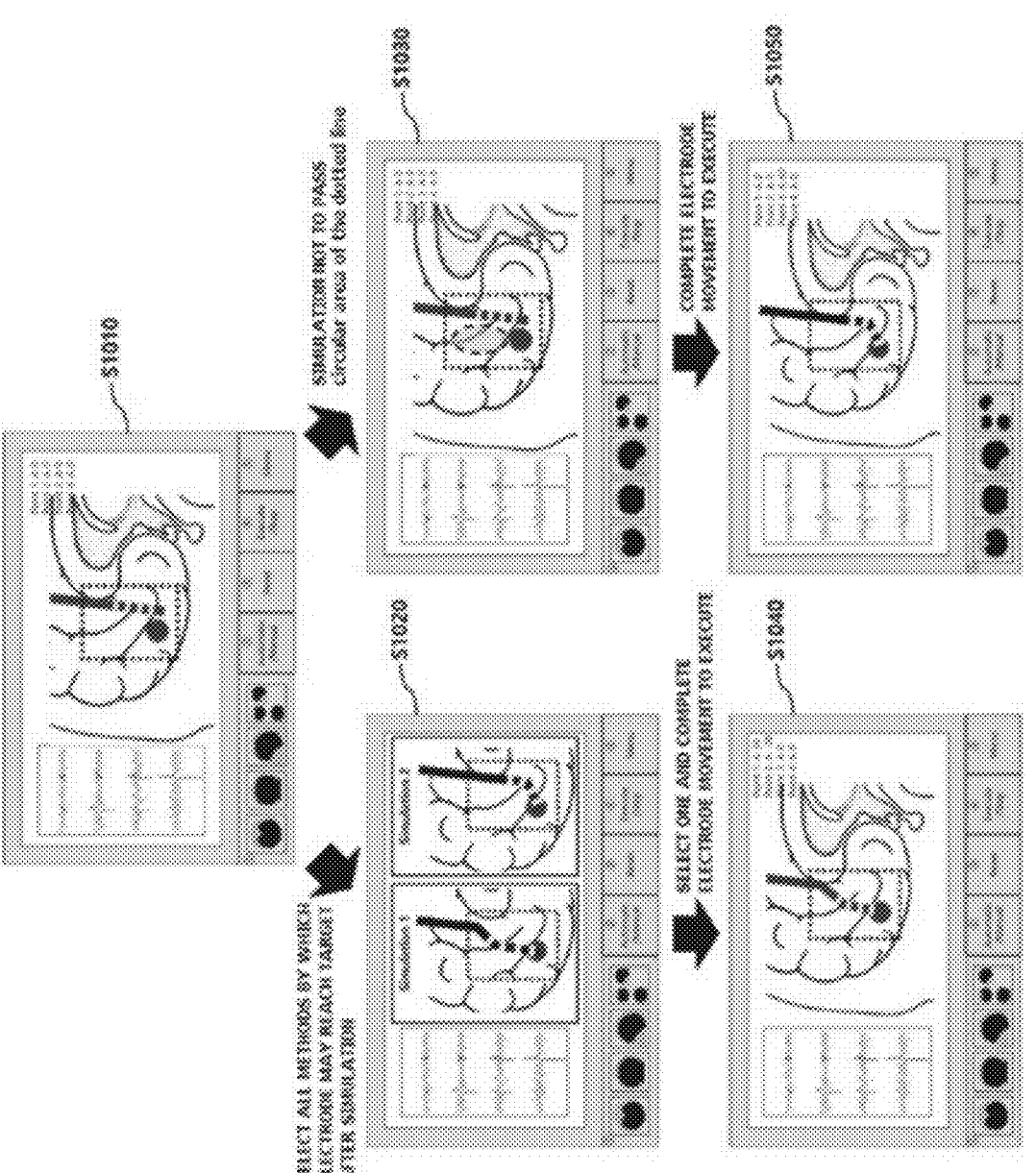
FIG. 10 is a pictorial view for explaining a simulation image performed in a method of controlling an implanted electrode according to an embodiment of the present invention.
Figure 11:
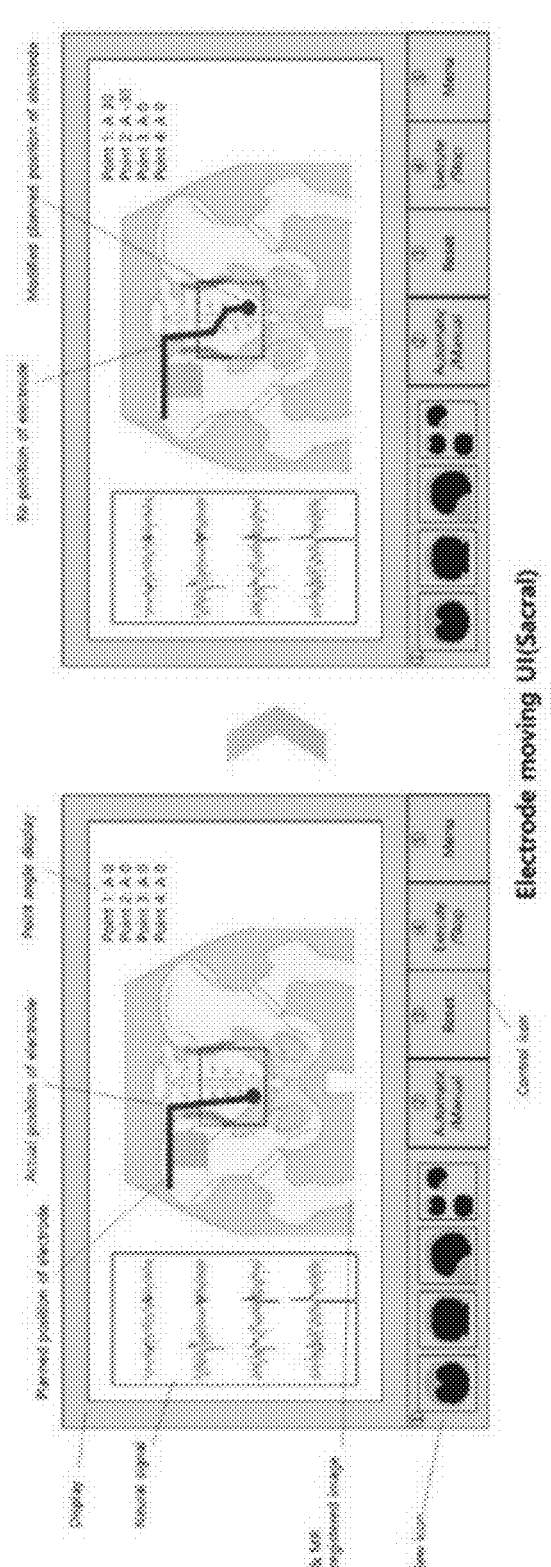
FIG. 11 is a pictorial view for explaining an image applied to the pelvis in addition to the brain by an implanted electrode control device according to an embodiment of the present invention.
Figure 12:
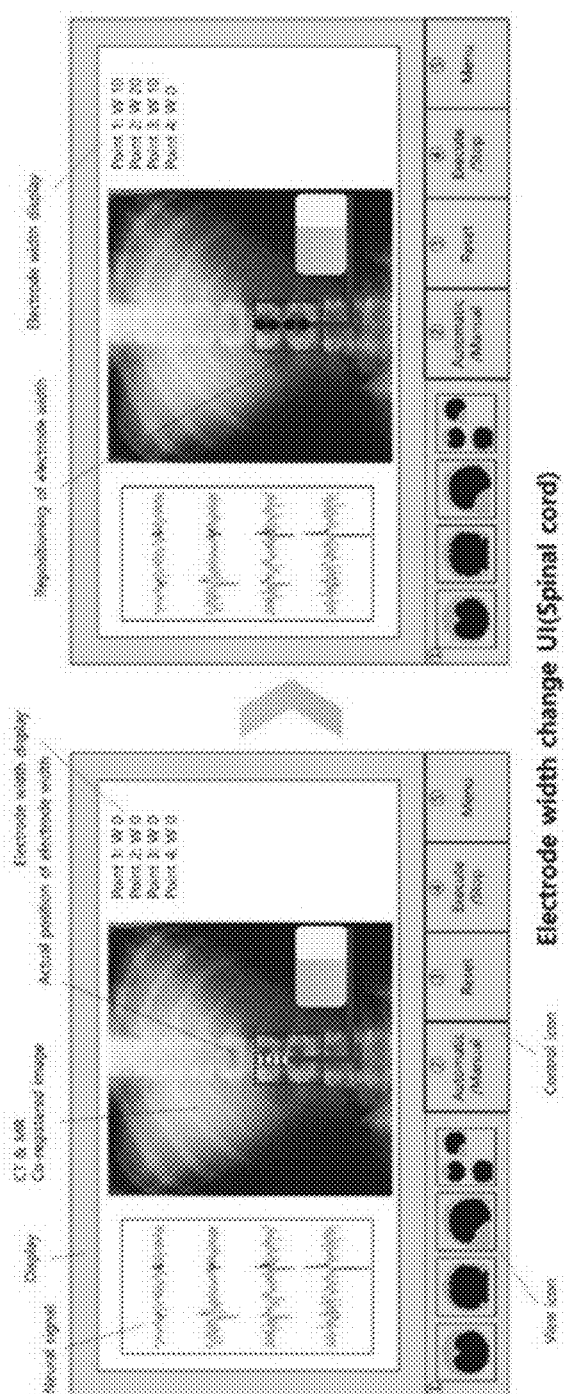
FIG. 12 is a pictorial view for explaining an image in which an implanted electrode control device according to an embodiment of the present invention is applied to the spine other than the brain.

FIG. 9 is a flowchart for explaining a method of controlling an implanted electrode according to another embodiment of the present invention, and FIG. 10 is a view for explaining a simulation image performed in a method of controlling an implanted electrode according to an embodiment of the present invention. FIG. 10 is for explaining a partial process of the flowchart shown in FIG. 9 and will be described together with FIG. 9.

Referring to FIG. 9, according to an embodiment, in operation S910, an implanted electrode control device may receive a target region into which an electrode is to be implanted and an implantation-prohibited region where electrode implantation is prohibited through a user interface. According to an embodiment, an electrode may include an electrode wire in which contact points of the electrode are movable.

According to an embodiment, an initial position of a pre-implanted electrode, an initial position of contact points of an electrode, and information about setting the type or model of an electrode to be used may be preset. In addition, before operation S910, communication connection with an external device that provides image information to the implanted electrode control device may be performed.

According to an embodiment, before operation S910, when the electrode adjustment unit 114 is connected to the communication unit 112 by wire, the communication unit 112 may be connected to the electrode adjustment unit 114 through an electrode clip.

According to an embodiment, in operation S920, the implanted electrode control device may calculate a distance and direction between a current position of an electrode and an implantation target region considering the implantation-prohibited region.

According to an embodiment, in operation S930, the implanted electrode control device may calculate a moving path of an electrode according to the type of the electrode and output a movement simulation image of the electrode including the calculated moving path. According to an embodiment, a neural signal obtained from an electrode may be transmitted to the control unit 111 in real time, and a position at which an electrode is implanted may be calculated by analyzing the neural signal and an image input from an external device.

According to an embodiment, in operation S940, the implanted electrode control device may receive the type of electrode through a user interface, and may determine a method of moving an electrode according to the type of the received electrode.

When the type of the received electrode is a general electrode ("Yes" of operation S951), in operation S961, the implanted electrode control device may extract a pre-implanted electrode and move the pre-implanted electrode in a distance and direction to an implantation target region.

When the type of the received electrode is a movable electrode ("Yes" of operation S952), in operation S962, the implanted electrode control device may locate the pre-implanted electrode in the implantation target region by bending the pre-implanted electrode in the distance and direction to the implantation target region.

When the type of the received electrode is an electrode with movable contact points ("Yes" of operation S953), in operation S963, the implanted electrode control device may increase or decrease a width between the contact points of the electrode so that the contact points of the electrode are located in the implantation target region.

According to an embodiment, in operation S970, the implanted electrode control device may calculate a moving path according to the method of moving an electrode, and output simulation of electrode movement according to a path calculated before electrode movement as an image.

According to an embodiment, the implanted electrode control device may enlarge a simulation image using a touch or mouse based on a simulated electrode position, and a user may precisely adjust an electrode position using the enlarged simulation image.

According to an embodiment, in operation S980, the implanted electrode control device may recheck whether an implantation-prohibited region is included as a path in a method of moving a simulation image. When the implantation-prohibited region is included as a path in the method of moving a simulation image ("Yes" of operation S980), a distance and direction to the implantation target region may be recalculated considering the implantation-prohibited region.

When the implantation-prohibited region is not included as a path in the method of moving a simulation image ("No" of operation S980), in operation S990, the implanted electrode control device may output a simulation image for an effective change in electrode position. A user may move an electrode to the implantation target region in real time by checking the corresponding simulation image. A user may see a real-time position of an electrode and a position of an electrode implantation region output on a screen and implant an electrode according to the existing electrode implantation order.

According to an embodiment, when the implantation target region is different from a region into which an electrode is actually implanted, the implanted electrode control device may output a simulation image that automatically simulates how much an electrode or contact points of the electrode need to move.

When the simulation image is output, a user may input an input value for actually moving an electrode according to a moving path of an electrode in the simulation image.

In relation to operations S970, S980, and S990, a process of outputting a simulation image will be described with reference to FIG. 10.

As a method of controlling an implanted electrode according to an embodiment, a method of simulating a moving path may include: a first method in which, when a plurality of simulation images for a moving path from a current electrode position to an implantation target region of an electrode are output, a user selects one of the plurality of simulation images (operations S1020 and S1040); a second method of selecting a moving path that does not include an implantation-prohibited region by checking whether an implantation-prohibited region that should not be included in a moving path of an electrode is included in a moving path(operations S1030 and S1050); and a third method of simulating a moving path of an electrode by setting a moving path of an electrode directly on a screen by a user.

The first method in which a user selects a moving path of an electrode according to one of the plurality of output simulation images has an advantage in that a user may select a moving path that moves efficiently while reducing internal injuries caused by electrode movement.

In the second method of selecting a moving path that does not include an implantation-prohibited region by checking whether an implantation-prohibited region is included in a moving path, because the implantation-prohibited region is a region through which blood vessels pass or a region that plays an important role in the brain, more stable electrode movement may be induced by excluding regions that may cause a major problem in the case of injury while moving an electrode from a moving path of an electrode.

By setting the implantation-prohibited region according to the second method, a user may directly mark a specific region, and may avoid a specific tissue by classifying tissues such as blood vessels, nerves, and bones by type using other image analysis algorithms.

The third method is a method capable of adjusting electrode movement more precisely after simulation of a moving path of an electrode is finished by the first method and the second method. According to the third method, electrode movement may be finely adjusted by reflecting a user's input regarding not only an electrode reaching an implantation target region of the electrode but also in which peripheral

The invention claimed is:

1. An implanted electrode control device comprising:
a communication unit configured to receive information including image information of a portion of a body of a patient from a plurality of external devices and neural signals from an implanted electrode;
an adjustment unit wirelessly coupled to the communication unit and configured to adjust a current position of the implanted electrode in the body of the patient, wherein the adjustment unit is implanted into the body of the patient;
a control unit wirelessly coupled to the communication unit and the adjustment unit and configured to determine, based on the received image information and the neural signals, a first region in the body in which the electrode is to be implanted and a second region in which electrode implantation is prohibited, to determine a plurality of predicted paths through which the electrode is moved based on the current position of the implanted electrode, the first region, and the second region, and to determine a type of electrode implanted into the body based on the received image information, wherein the control unit analyzes the neural signals, determines a stimulation position within the first region into which the electrode is implanted, and commands the adjustment unit, via the communication unit, to move the implanted electrode over the plurality of predicted paths to the stimulation position; and
an output unit configured to output the current position of the implanted electrode, the plurality of predicted paths, the type of the implanted electrode, and the stimulation position;
wherein the adjustment unit is operated by the control unit for selectively adjusting the position of the implanted electrode after completion of a procedure for implantation of the electrode and the adjustment unit into the body of the patient;
wherein the predicted paths through which the implanted electrode is moved includes a changed direction of the implanted electrode; and
wherein the changed direction of the implanted electrode is provided by bending a portion of the electrode in a direction toward the first region;

wherein the plurality of external devices providing the image information to the communication unit comprise one or more of a video electroencephalography (EEG) device, a magnetic resonance imaging (MRI) examination device, a single-photon emission computed tomography (SPECT) examination device, a positron emission tomography (PET) device, a magnetoencephalography (MEG) device, or a C-arm device;

wherein when the operation for selectively adjusting the position of the implanted electrode terminates, the control unit releases a wireless communication connection with the communication unit.

2. The implanted electrode control device of claim 1, wherein the communication unit receives the type of electrode implanted into a body.

3. The implanted electrode control device of claim 1, wherein the control unit identifies a real-time position of an electrode pre-implanted into the body based on the received information, and the output unit outputs the identified real-time position of the electrode.

4. The implanted electrode control device of claim 1, wherein the control unit determines each of the plurality of predicted paths differently based on a model of the electrode and the type of electrode.

5. The implanted electrode control device of claim 4, wherein the calculated different predicted paths include at least one of a changed depth of the electrode, the changed direction of the electrode, or a changed position of a contact point of the electrode.

6. The implanted electrode control device of claim 1, wherein the type of the electrode is comprised of an electrode providing electrical stimulation to the first region in the body.

7. The implanted electrode control device of claim 6, wherein the type of the electrode includes one of an electrode in which a contact point of the electrode is changeable, an electrode in which a position of the electrode is movable, and an electrode in which a contact point of the electrode is movable.

8. The implanted electrode control device of claim 1, wherein the adjustment unit includes an electrode clamp.

* * * * *